United States Patent [19]

Nunn et al.

[11] 4,418,208

[45] Nov. 29, 1983

[54] N-SUBSTITUTED IMINODIACETIC ACIDS

[75] Inventors: Adrian Nunn, Hopewell; Michael Loberg, Princeton, both of N.J.

[73] Assignee: E. R. Squibb & Sons, Inc., Princeton, N.J.

[21] Appl. No.: 388,795

[22] Filed: Jun. 16, 1982

Related U.S. Application Data

[63] Continuation of Ser. No. 221,155, Dec. 29, 1980, abandoned.

[51] Int. Cl.$^3$ .................... C07C 101/20; A61K 49/00
[52] U.S. Cl. .................... 562/449; 424/1.1; 562/450
[58] Field of Search .................... 562/449, 450

[56] References Cited

U.S. PATENT DOCUMENTS

| | | | |
|---|---|---|---|
| 3,725,295 | 4/1973 | Eckelman et al. | 562/449 |
| 4,017,596 | 4/1977 | Loberg et al. | 562/449 |
| 4,316,883 | 2/1982 | Schrijver | 562/433 |

FOREIGN PATENT DOCUMENTS 855107 11/1977 Belgium .................... 562/449

OTHER PUBLICATIONS

Wiston et al, Radio Chem & Radiopharmaceuticals, vol. 18, pp. 455–461 (1977).
3rd Int. Sym. Radiopharm. Chem., St. Louis, Mo., Jun., 1980 (paper presented by Molter et al).
Journal of Labeled Compounds and Radiopharmaceuticals, XV: 387–399 (1978).
Radiology, 128:793:794 (1978).
Eur. J. Nucl. Med., 4:445–448 (1979).
Int. J. Nucl. Med., Biol., 7:1–7 (1980).

Primary Examiner—James H. Reamer
Attorney, Agent, or Firm—Lawrence S. Levinson; Donald J. Barrack

[57] ABSTRACT

Complexes of technetium-99m and a compound selected from the group having the formula $$\underset{R_3 \quad R_4}{\underset{R_2}{\overset{R_1}{\text{Ar}}}}-(CH_2)_n-NH-\overset{O}{\overset{\|}{C}}-CH_2-N\underset{CH_2-\overset{\|}{\underset{O}{C}}-OH}{\overset{CH_2-\overset{\|}{\underset{O}{C}}-OH}{\diagup}}$$

or a pharmaceutically acceptable, water soluble salt thereof wherein $R_1$ and $R_4$ are each independently hydrogen, methyl or ethyl;

one of $R_2$ and $R_3$ is alkyl of 1 to 4 carbons and the other is bromine or iodine; and n is 0, 1 or 2, are useful for the external imaging of the hepatobiliary system.

9 Claims, No Drawings

N-SUBSTITUTED IMINODIACETIC ACIDS

This is a continuation of application Ser. No. 221,155, filed Dec. 29, 1980 now abandoned.

BACKGROUND OF THE INVENTION

With the exception of the brain, the liver is the organ most frequently examined by nuclear medicine procedures. Most of these studies involve the intravenous administration of labeled particles such as Tc-99m sulfur colloid which are effectively trapped by the Kupffer cells. The diagnostic information thus obtained is useful for studying liver morphology and Kupffer cell function. The optimum agent for these studies would have rapid, exclusive uptake into healthy Kupffer cells and would be biodegradeable and non-toxic.

Radionuclide studies are also used to measure hepatocyte function and bile duct patency (including gallbladder function). The optimum agent for these studies would have rapid, exclusive uptake by the hepatocytes, rapid intrahepatic transit, and prompt excretion into the biliary system. High specificity is required to obtain maximum diagnostic information while limiting patient radiation dose. The time to maximum liver concentration ($t_{max}$) and the time for the liver concentration to decrease to 50% of the concentration at $t_{max}$ ($t_{50}$) should both be short to reduce the time required for a study. This is important in patients that cannot be immobilized for long periods of time. Shorter study times increase the number of patients that can be handled in a given period of time maximizing the use of imaging equipment. A short $t_{50}$ also means an increase in the ratio of radioactivity within the bile to that within the liver, thereby resolving the intrahepatic ducts from the liver and thus improving the quality of the image and of the resultant diagnosis.

Until recently, most of the nuclear medicine biliary function studies were performed with I-131 rose bengal or I-131 bromosulfophthalein. Although I-131 rose bengal is usually the standard for comparing liver function agents, its photon energy is not optimum for gamma camera imaging, and the patient exposure to non-diagnostic beta radiation limits the dose which can safely be administered. Image resolution and, therefore, diagnostic information is limited.

The development of Tc-99m penicillamine by Tubis e al (*Radiopharmaceuticals*, Subramanian et al, eds., The Society of Nuclear Medicine, Inc., New York, 1975, pgs 55–62) in 1974 was a significant step in overcoming the limitations of the iodine-131 label and in stimulating research interest in technetium-99m labeled hepatobiliary agents. Among the most useful technetium-99m labeled agents developed to date are the N-substituted iminodiacetic acids (hepatoiminodiacetic acids- HIDA's). Loberg et al., in U.S. Pat. No. 4,017,596 disclose, inter alia, the use of a chelate of technetium-99m and a substituted iminodiacetic acid for external organ imaging. Eckelman et al., in U.S. Pat. No. 3,725,295 disclose the labeling of diethylenetriaminepentaacetic acid (DPTA) with technetium-99m.

The various HIDA derivatives which have been disclosed in the literature can be represented by the formula

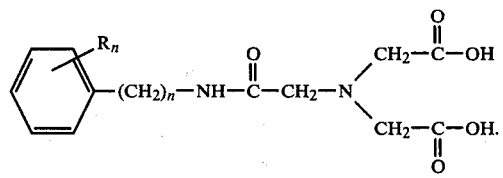

The analogs discussed include the 2,6-dimethyl derivative (Loberg et al., U.S. Pat. No. 4,017,596); 2,6-diethyl, 2,6-diisopropyl, 2-butoxy, 4-butoxy, 4-butyl, 4-isopropyl, 4-ethoxy and 4-iodo derivatives (Wistow et al., *Radiology*, 128:793–794, 1978 and *J. Nucl. Med.*, 18(5):455–461, 1977); 2,3-dimethyl, 2,4-dimethyl, 2,5-dimethyl, 3,4-dimethyl and 3,5-dimethyl derivatives (Van Wyk et al., *Eur. J. Nucl. Med.*, 4:445–448, 1979); and 2,4,6-trisubstituted derivatives wherein at least two of the substituents are alkyl of 1 to 4 carbons, the third substituent is hydrogen or alkyl of 1 to 4 carbons, and together the substituents contain at least three carbons (Belgian patent No. 855,107); and 2,6-dimethyl, 2,6-diethyl, 2,6-diisopropyl, 4-methyl, 4-ethyl, 4-isopropyl, 4-n-butyl, 4-n-pentyl, 4-t-butyl, 4-phenyl, 4-methoxy, 3,5-dimethyl, 2,4,6-trimethyl, 2,4,5-trimethyl, 4-fluoro, 2,4-difluoro, 2,5-difluoro, and 2,3,4,5,6-pentafluoro derivatives (Molter et al., 3rd Int. Symp. Radiopharm. Chem., St. Louis, Mo., June 1980). Fields et al, *Journal of Labelled Compounds and Radiopharmaceuticals*, XV: 387–399 (1978) disclose N-(2-phenethylcarbamoylmethyl)iminodiacetic acid. p Van Wyk et al., *Eur. J. Nucl. Med.*, 4:445–448, 1979, in their work with dimethyl HIDA derivatives have shown that steric effects of substituents are important for biliary uptake. Chiotellis et al., *Int. J. Nucl. Med. Biol.*, 7:1–7, 1980, working with 4-butyl HIDA compounds, have shown that molecular size of substituents is important for biliary uptake.

BRIEF DESCRIPTION OF THE INVENTION

Complexes of technetium-99m and a compound selected from the group having the formula $$\text{R}_2\underset{\underset{\text{R}_3}{|}}{\overset{\overset{\text{R}_1}{|}}{\bigodot}}\text{R}_4 - (\text{CH}_2)_n - \text{NH} - \overset{\text{O}}{\underset{||}{\text{C}}} - \text{CH}_2 - \text{N} \begin{matrix} \text{CH}_2 - \overset{\text{O}}{\underset{||}{\text{C}}} - \text{OH} \\ \text{CH}_2 - \underset{||}{\overset{\text{O}}{\text{C}}} - \text{OH}, \end{matrix} \quad \text{I}$$

or a pharmaceutically acceptable water soluble salt thereof, are useful for the external imaging of the hepatobiliary system. The complexes have good specificity (i.e., when injected into a mammal a large percentage of the complex passes through the liver into the bile) and they exhibit rapid transport from liver to bile allowing for good biliary measurements. In formula I, and throughout the specification, the symbols are as defined below.

$R_1$ and $R_4$ are each independently hydrogen, methyl or ethyl;

one of $R_2$ and $R_3$ is alkyl of 1 to 4 carbons and the other is bromine or iodine; and $n$ is 0, 1 or 2.

This invention encompasses the compounds of formula I (and salts thereof) and compositions comprising the compounds of formula I (and salts thereof) and a reducing agent, which are suitable for complexing with technetium-99m.

DETAILED DESCRIPTION OF THE INVENTION

Compounds of formula I, and salts thereof, can be labeled with technetium-99m and subsequently administered intravenously into a patient for the purpose of imaging the hepatobiliary system. The radiolabeling of compounds of formula I, and salts thereof, can be accomplished using procedures well known in the art. In a preferred procedure, technetium-99m in the form of an aqueous sodium pertechnetate solution (Na99mTcO4) is combined with a reducing agent and a compound of formula I, or salt thereof. While the order of mixing of the three above-described components is not critical it is most preferred that the reducing agent be first combined with a compound of this invention. This composition (a non-radioactive composition) can then be supplied to radiochemists, technicians, radiopharmacists, doctors and the like for labeling with technetium-99m just prior to use.

Stannous ion is the preferred reducing agent. Exemplary stannous reducing agents are stannous chloride and stannous fluoride. Technetium-99m in the form of an aqueous solution of sodium pertechnetate is readily obtainable from commercially available molybdenum-99/technetium-99m generators which are conventionally eluted with saline.

The compounds of this invention can be prepared using as starting materials nitrilotriacetic acid, acetic anhydride, and an amine derivative having the formula

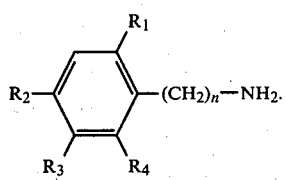

Nitrilotriacetic acid and acetic anhydride are first reacted to give nitrilotriacetic anhydride which is then reacted with an amine of formula II to give the corresponding compound of formula I. The reactions proceed most readily if the reactants are present in stoichiometric amounts.

The compounds of formula I can be converted to pharmaceutically acceptable, water-soluble salts using art-recognized procedures. Preferred salts are alkali metal salts and alkaline earth metal salts.

The compounds of formula I (and salts thereof) can be prepared for complexing with technetium-99m using art-recognized procedures. For example, a "wet kit" can be prepared by first dissolving a compound of formula I (or salt thereof) in base (e.g., sodium hydroxide) to give a solution of about pH 6 to 7. To this solution is added an acidic solution of reducing agent (e.g., stannous fluoride) in hydrochloric acid. Water can be added to give the desired volume. To this solution technetium-99m, preferably an aqueous solution of sodium pertechnetate, can be added. Lyophilized kits can be prepared using the above-described procedure, except that prior to the addition of technetium-99m the solution is lyophilized. The lyophilized material may be stored in an inert atmosphere.

Preferred compounds of this invention are those compounds of formula I wherein n is 0. Particularly preferred are those compounds having the formula

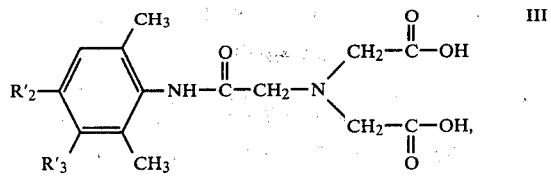

or a pharmaceutically acceptable, water soluble salt thereof, wherein one of $R_2'$ and $R_3'$ is methyl or ethyl and the other is bromine or iodine.

The following examples are specific embodiments of this invention.

EXAMPLE 1

2,2'-[[2-[(3-bromo-2,4,6-trimethylphenyl)amino]-2-oxoethyl]imino]bisacetic acid (A) 3-Bromo-2,4,6-trimethylaniline Concentrated hydrochloric acid (80 ml) is cooled in an ice-water bath to 5° C. 2,4,6-Trimethylaniline (13.5 g) is added over a period of 20 minutes with vigorous stirring while keeping the temperature below 15° C. The thick slurry is cooled to 3° C. and 16.8 g of bromine in 80 ml of concentrated hydrochloric acid is added over a period of 25 minutes. The slurry is heated in a water bath for one hour and then cooled in an ice bath for one hour. The reaction mixture is then filtered and the salt is washed with three 50 ml portions of cold distilled water. After drying, the crude product is dissolved in 600 ml of distilled water, treated with 3.0 g of Darco and filtered on a Hyflo-bed to give a solution. Neutralization with concentrated ammonium hydroxide gives a milky solution from which the product solidifies upon cooling to 10° C. After refrigeration for about 16 hours, the tan product is filtered, washed with cold distilled water and dried under vacuum for about 16 hours to give 12.0 g of the title compound, melting point 34.0°–35.0° C.

(B) 2,2'-[[2-[(3-bromo-2,4,6-trimethylphenyl)amino]-2-oxoethyl]]imino]bisacetic acid A suspension of 9.56 g of nitrilotriacetic acid in pyridine (dried over molecular sieves) is prepared with the exclusion of moisture (CaSO4 drying tube) and heated to 50° C. Acetic anhydride (5.11 g) is added dropwise. The reaction mixture clears and is heated to 100° C. After maintaining the temperature for 40 minutes, the reaction mixture is cooled to 55° C. and a solution of 10.7 g 3-bromo-2,4,6-trimethylaniline in 25 ml of dry pyridine is added slowly. The reaction is heated to 100° C. and after 1.5 hours at this temperature, the solution is cooled in an ice-bath. The reaction mixture is rotary evaporated to a semisolid which is dissolved in 125 ml of 10% sodium hydroxide w/v. The basic layer is then extracted with two 100 ml portions of methylene chloride. Distilled water (100 ml) is added to the basic layer which is then brought to pH 3 with concentrated hydrochloric acid to give a precipitate. After refrigeration for about 16 hours, the crude product is filtered, washed with cold distilled water and dried under vacuum at 40° C. The crude product is dissolved in 100 ml of 60% aqueous ethanol, treated with 3.0 g of Darco and filtered hot through a Hyflo-bed to give a solution. Crystals precipitate and are filtered, washed with three 25 ml portions of 50% aqueous ethanol and dried under vacuum at 40° C. The reaction yields 9.1 g of the title compound, melting point 198°-200° C., dec.

EXAMPLE 2

2,2'-[[2-[(3-[(3-Bromo-2,6-diethyl-4-methylphenyl)-amino]-2-oxoethyl]imino]bisacetic acid (A) 3-Bromo-2,6-diethyl-4-methylaniline Concentrated HCl (10 ml) is cooled to 5° C. in an ice-water bath and 1.63 g of 2,6-diethyl-4-methylaniline is added dropwise to give a slurry. Bromine (1.59 g) with 10 ml of concentrated HCl is added dropwise over 30 minutes. The reaction is allowed to stir for 3.75 hours and 25 ml of distilled water is added. After cooling for 1.0 hour, the reaction mixture is filtered and washed twice with 25 ml of cold distilled water. After drying under vacuum for about 16 hours, the crude solid (2.3 g) is dissolved in 100 ml of 10% NaOH and extracted with a 150 ml portion and with a 100 ml portion of methylene chloride. After drying over sodium sulfate, the methylene chloride solution is rotary evaporated to 1.9 g of crude product.

(B)
2,2'-[[2-[(3-Bromo-2,6-diethyl-4-methylphenyl)-amino]-2-oxoethyl]imino]bisacetic acid A slurry of 1.34 g of nitrilotriacetic acid in 15 ml of dry pyridine (dried over molecular sieves) is prepared and heated to 46° C. Acetic anhydride (0.72 g) is added (1 ml pyridine rinse) and the solution is heated to 100° C. After heating for 0.5 hour, the solution is allowed to cool to 46° C. and a solution of 1.7g of crude 3-bromo-2,6-diethyl-4-methylaniline in 6 ml of pyridine is slowly added. The solution is heated at 100° C. for 2 hours, cooled, and rotary evaporated to a pasty product. The product is dissolved in 25 ml of 10% sodium hydroxide and the resulting solution is extracted twice with 25 ml portions of methylene chloride. The aqueous solution is diluted with 50 ml of distilled water, neutralized with concentrated HCl to pH 3.0, and refrigerated for about 16 hours. Filtration gives a solid which upon drying for 3 hours at 60° C. under vacuum gives 1.4 g of crude product. Recrystallization from 25 ml of 50% ethanol gives 1.04 g of needles, melting point 194.5°-195.5° C.

EXAMPLE 3

2,2'-[[2-[(3-Iodo-4-methylphenyl)amino]-2-oxoethyl]-imino]bisacetic acid

A slurry of 4.78 g of nitrilotriacetic acid in 40 ml of dry pyridine (dried over molecular sieves) is heated to 60° C. Acetic anhydride (2.55 g) is added slowly and the solution is heated to 100° C. After heating for 0.5 hour, the solution is cooled to 40° C. and a solution of 5.8 g of 3-iodo-4-methylaniline in 20 ml of dry pyridine is added over 25 minutes. The solution is heated at 100° C. for 1.0 hour. The reaction is cooled and rotary evaporated to a residue which is dissolved in 65 ml of 10% sodium hydroxide. This solution is extracted twice with 50 ml portions of methylene chloride diluted with 100 ml of distilled water, and neutralized with concentrated HCl to pH 3.2. The crude product is refrigerated for about 16 hours, filtered, washed twice with 50 ml portions of distilled water, and dried under vacuum at 40° C. The crude product (8.0 g) is recrystallized after Darco treatment to yield 5.7 g of product, melting point 213.5°-215.0° C. (dec).

EXAMPLE 4

2,2'-[[2-[(4-Bromo-3-methylphenyl)amino]-2-oxoethyl]imino]bisacetic acid

A slurry of 9.56 g of nitrilotriacetic acid in 80 ml of dry pyridine (dried over molecular sieves) is heated to 55° C. Acetic anhydride (7.66 g) is added and the solution is heated to 100° C. After heating for 0.5 hour, the solution is cooled to 55° C. and 9.30 g of 4-bromo-3-methylaniline is added with a 5 ml pyridine rinse. The solution is heated at 100° C. for 1.0 hour. The reaction is cooled and rotary evaporated to a pasty solid which is dissolved in 120 ml of aqueous ammonium hydroxide (30 ml concentrated ammonium hydroxide/90 ml distilled water). The clear brown solution is extracted with two 100 ml portions of methylene chloride and neutralized to pH 3 with 35 ml of concentrated HCl. The white solid is filtered, washed with three 25 ml portions of cold distilled water, and dried under vacuum for 2.75 hours at 60° C. The crude product (12.9 g) is recrystallized from 360 ml of 50% ethanol to give 9.85 g of product, melting point 206.5°-209.0° C.

EXAMPLE 5

2,2'-[[2-[(3-Bromo-4-methylphenyl)amino]-2-oxoethyl]-imino]bisacetic acid

A slurry of 4.78 g of nitrilotriacetic acid in 40 ml of dry pyridine (dried over molecular sieves) is prepared and heated to 50° C. Acetic anhydride (2.55 g) is added slowly and the solution is heated to 100° C. After heating for 0.5 hour, the solution is cooled to 42° C. and 4.81 g of 3-bromo-4-methylaniline in 5 ml of pyridine is slowly added. The solution is heated to 100° C. After heating for 2.0 hours, the reaction is cooled and rotary evaporated. This material is dissolved in 75 ml of 10% sodium hydroxide, and extracted twice with 50 ml portions of methylene chloride. The aqueous portion is diluted with 100 ml of distilled water, neutralized to pH 3.2 with concentrated HCl, and refrigerated for about 16 hours overnight. The reaction is filtered and washed with cold distilled water. After drying for 3 hours under vacuum at 60° C., 7.14 g of crude product is obtained, melting point 206.0°-208.0° C. Recrystallization from 150 ml of 75% ethanol gives 6.4 g of solid, melting point 209.0°-210.0° C.

EXAMPLE 6

Formulations for complexing with technetium-99m

The table below presents exemplary formulations of compounds of formula I with stannous fluoride reducing agent. The formulations are prepared by dissolving the ligand in 0.46 M sodium hydroxide to give a solution of final pH of about 6 to 7.5. To this is added 0.01 ml of a 70 mg/ml solution of stannous fluoride in 6 M hydrochloric acid and the volume is brought to 5 ml with water for injection. The formulations in the following table have a preferred molar ratio of ligand:tin of 150:1.

TABLE

| | Concentration (mg/ml) | | |
|---|---|---|---|
| Ligand | ligand | stannous fluoride | pH |
| 2,2'-[[2-[(3-Bromo-2,4,6-trimethylphenyl)-amino]-2- | 48.6 | 0.14 | 6.76 |

TABLE-continued

| Ligand | Concentration (mg/ml) stannous ligand | fluoride | pH |
|---|---|---|---|
| oxoethyl]imino]bisacetic acid | | | |
| 2,2'-[[2-[(3-[(3-Bromo-2,6-diethyl-4-methylphenyl)amino]-2-oxoethyl]imino]bisacetic acid | 51.9 | 0.14 | 5.99 |
| 2,2'-[[2-[(3-Iodo-4-methylphenyl)amino]-2-oxoethyl]imino]bisacetic acid | 50.4 | 0.14 | 7.55 |
| 2,2'-[[2-[(4-Bromo-3-methylphenyl)amino]-2-oxoethyl]imino]bisacetic acid | 44.6 | 0.14 | 5.96 |
| 2,2'-[[2-[(3-Bromo-4-methylphenyl)amino]-2-oxoethyl]imino]bisacetic acid | 44.9 | 0.14 | 7.39 |

What is claimed is:

1. A compound having the formula

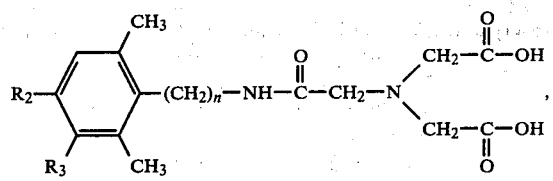

or a pharmaceutically acceptable, water soluble salt thereof, wherein one of $R_2$ and $R_3$ is methyl and the other is bromine and n is 0, 1 or 2.

2. A compound in accordance with claim 1 wherein n is 0.

3. A compound having the formula

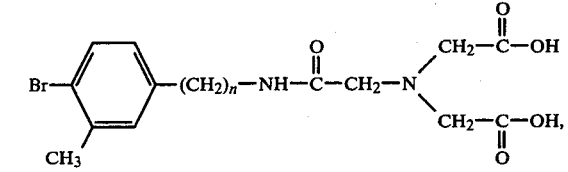

or a pharmaceutically acceptable, water soluble salt thereof, wherein n is 0, 1 or 2.

4. A composition comprising a stannous reducing agent and a compound having the formula

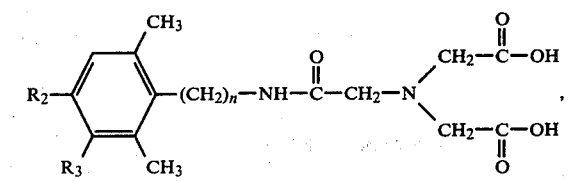

or a pharmaceutically acceptable, water soluble salt thereof, wherein one of $R_2$ and $R_3$ is methyl and the other is bromine and n is 0, 1 or 2.

5. A composition in accordance with claim 4 wherein n is 0.

6. A composition comprising a stannous reducing agent and a compound having the formula

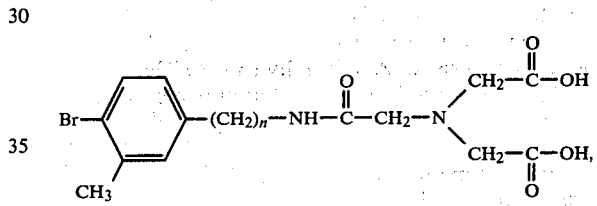

or a pharmaceutically acceptable, water soluble salt thereof, wherein n is 0, 1 or 2.

7. A composition in accordance with claim 6 wherein n is 0.

8. The compound in accordance with claim 2, 2,2'-[[2-[(3-bromo-2,4,6-trimethylphenyl)amino]-2-oxoethyl]imino]bisacetic acid.

9. The compound in accordance with claim 3, 2,2'-[[2-[(4-bromo-3-methylphenyl)amino]-2-oxoethyl]imino]bisacetic acid.

* * * * *

UNITED STATES PATENT AND TRADEMARK OFFICE

CERTIFICATE EXTENDING PATENT TERM
UNDER 35 U.S.C. 156

Patent No.    : 4,418,208

Dated         : November 29, 1983

Inventor(s)   : Adrian Nunn, et al

Patent Owner  : E.R. Squibb & Sons, Inc.

This is to certify that there has been presented to the

COMMISSIONER OF PATENTS AND TRADEMARKS an application under 35 U.S.C. 156 for an extension of the patent term. Since it appears that the requirements of law have been met, this certificate extends the term of the patent for the period of

53 DAYS with all rights pertaining thereto as provided by 35 USC 156(b).

I have caused the seal of the Patent and Trademark Office to be affixed this Twenty-second day of December 1987.

Donald J. Quigg

Assistant Secretary and Commissioner of Patents and Trademarks